United States Patent

Blomström et al.

[11] Patent Number: 6,100,441
[45] Date of Patent: *Aug. 8, 2000

[54] MATERIAL HAVING A HIGH ABSORPTIVE CAPACITY AND AN ABSORBENT STRUCTURE, AND AN ABSORBENT PRODUCT WHICH INCLUDES THE MATERIAL IN QUESTION

[75] Inventors: Peter Blomström, Stenungssundsgatan; Anette Buschka, Träringen, both of Sweden

[73] Assignee: SCA Hygiene Products AB, Gothenburg, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/860,566
[22] PCT Filed: Dec. 15, 1995
[86] PCT No.: PCT/SE95/01521
  § 371 Date: Jun. 30, 1997
  § 102(e) Date: Jun. 30, 1997
[87] PCT Pub. No.: WO96/20667
  PCT Pub. Date: Jul. 11, 1996

[30] Foreign Application Priority Data

Dec. 30, 1994 [SE] Sweden .................................. 9404578

[51] Int. Cl.[7] ..................................................... A61F 13/20
[52] U.S. Cl. .......................... 604/367; 604/368; 604/375; 428/221
[58] Field of Search ..................................... 162/100, 142, 162/158; 604/367, 368, 374, 375, 378; 428/171, 172, 221, 224, 283

[56] References Cited

U.S. PATENT DOCUMENTS

| | | | |
|---|---|---|---|
| 4,822,453 | 4/1989 | Dean et al. | 162/158 |
| 4,865,596 | 9/1989 | Weisman et al. | 604/368 |
| 4,898,642 | 2/1990 | Moore et al. | 604/375 |
| 4,935,022 | 6/1990 | Lash et al. | 604/368 |
| 5,262,005 | 11/1993 | Eriksson et al. | 162/100 |
| 5,360,420 | 11/1994 | Cook et al. | 604/378 |
| 5,531,728 | 7/1996 | Lash | 604/378 |

FOREIGN PATENT DOCUMENTS

WO 90/05808  5/1990  WIPO .

*Primary Examiner*—Wynn Wood Coggins
*Assistant Examiner*—David J. Cho
*Attorney, Agent, or Firm*—Young & Thompson

[57] ABSTRACT

A material having a high absorptive capacity, for use in an absorbent product, such as a sanitary towel, tampon, incontinence protection, and nappy produced by a highly compressed cellulose-based absorptive material in reel form being finely divided into fragments, and included as a component having a high absorptive capacity in the absorbent structure within the absorbent product, displays good absorptive and swelling properties such as a high assimilation capacity and a high degree of surface dryness the absorbent structure may also contain conventional fluff cellulose pulp and binding fibers.

20 Claims, 3 Drawing Sheets

MATERIAL HAVING A HIGH ABSORPTIVE CAPACITY AND AN ABSORBENT STRUCTURE, AND AN ABSORBENT PRODUCT WHICH INCLUDES THE MATERIAL IN QUESTION

BACKGROUND

The present invention relates to a material having a high absorptive capacity for use in an absorbent structure in an absorbent product, such as a sanitary towel, tampon, nappy and the like, and also to an absorbent product which includes such an absorbent structure.

Absorbent products of this nature are known in a number of embodiments. Conventionally, the absorptive body in these products is produced by cellulose pulp, in rolls, bales or sheets, for example, being dry-defibred and converted, in fluff form, into a pulp mat, sometimes together with admixture of so-called superabsorbents, which are highly absorbent materials having the ability to absorb several times their own weight of water or body liquid.

The absorptive body can also contain further constituents, for example in order to improve its liquid-assimilating properties or its liquid-dispersing properties, or to increase its cohesiveness and ability to resist deformation during use.

In the case of most hygiene products, it is desirable for the product to be thin so that it can be worn as discretely as possible. In order to achieve this, the pulp body is often compressed, partly in order to reduce its bulk and partly in order to increase its liquid-dispersing ability.

A major problem with these products is that of combining the need to make a thin product with the need to have a high overall absorptive capacity. A substantially greater absorptive capacity can be achieved by adding highly-absorbent material to the absorptive body. A method of adding highly absorbent material to an absorbent structure is described in European Patent 122 042, in which a mixture of hydrophilic fibres and superabsorbent particles is air-laid to form a web and compressed to a density of from 0.15 to approximately 1.0 g/cm$^3$. The superabsorbent material is normally available in the form of granules or small particles which can be difficult to bind satisfactorily to the absorbent structure. Superabsorbent materials are also expensive, for which reason other solutions have been sought. Furthermore, the majority of superabsorbents are produced from synthetic, non-biodegradable polymers, for example polyacrylates. There is a need, therefore, for materials which have a high absorptive capacity and which at the same time are biodegradable.

Another problem with hygiene articles is that of so-called rewetting, i.e. when body liquid which has already been absorbed is pressed back towards the skin of the user by external influence, for example when the user sits down. It is, thus, a general requirement that the side of the product facing the user should be as dry as possible. By means of selecting absorbent materials which bind the absorbed liquid to a high degree, this problem can be reduced.

Another problem with absorbent structures in hygiene articles is that, at the high densities which are advantageous for liquid dispersal, it tends to be difficult to make such structures sufficiently soft and flexible to meet the high present-day demands for comfort in relation to this type of article.

Another problem with absorbent structures in hygiene articles is that of achieving high speeds of absorption and rapid assimilation of liquid, especially when repeated wetting occurs. When conventional super-absorbents are used, gel blocking can easily occur in the material, and the speed of absorption decreases with repeated wetting. There has therefore been a demand for highly absorbent materials which do not have any gel blocking tendency.

It is known from European Patent EP 444 073 to use dry forming in order to manufacture web-shaped pulp for subsequent defibering, so-called dry-formed reel pulp. The strength of the pressed web of flash-dried fibres, having a grammage of 300–1500 g/m$^2$ and a density of 550–1000 kg/m$^3$, is such that the web can be rolled up or handled in sheet form for storage and transport. It is easy to defibre and is normally meant to be converted into fluff form in order to be used for producing absorptive bodies in nappies, sanitary towels and similar products.

DESCRIPTION OF THE INVENTION

As has been previously mentioned, properties which are important for a highly absorbent material in a hygiene product include absorptive speed, absorptive capacity and retentive capacity. In addition, softness and flexibility are important. The principal liquids which are to be absorbed are urine, menstrual blood and blood.

The object of the present invention is to produce a material having a high absorptive capacity for use in an absorbent structure, in an absorbent product, of the type mentioned at the outset. The material should contribute to the product having a high absorptive speed with rapid assimilation of liquid, especially when repeated wetting occurs. The material should also impart to the product the ability to absorb large quantities of liquid and to bind the liquid in the material; it should ensure that the product exhibits a low degree of rewetting and should enable the product to be very thin, as well as soft and flexible, while retaining a high absorptive capacity. Furthermore, there is a need for the material to have a cost advantage over currently available superabsorbent materials. A further requirement is to produce a highly absorbent absorptive body which is entirely or in the main based on a biodegradable material, for example cellulose fibre.

The specified requirements have been achieved by the invention, by means of the material of high absorptive capacity consisting of fragments, having a length and width of in the main 1–5 mm, of a sheet of a dry-formed material which has a grammage of 100–1000 g/m$^2$, which contains at least 70% flash-dried cellulose fibres and which has a density of between 0.4–1.2 g/cm$^3$. The material has subsequently been incorporated, as a part of an absorbent structure, into an absorbent product. The absorbent product then displays, inter alia, a high absorptive capacity while at the same time retaining its flexibility and agreeable comfort properties. In this context, the fragments of dry-formed material can constitute the whole of the absorbent material in the absorbent product or be mixed with other types of absorbent material, for example conventional defibred and fluffed cellulose fibres. A suitable quantity of fragments of dry-formed material is 10–80%, preferably 20–50% and most preferably 30–40%.

Since the material having a high absorptive capacity is in the form of fragments having a length and width of in the main 1–5 mm, it can readily be incorporated into absorbent products of different shapes, for example body-contoured sanitary towels or nappies. The material can also be readily incorporated into absorbent products of a different type, for example tampons.

For the present invention, use is made of a dry-formed product which is manufactured from mechanical pulp or chemithermomechanical pulp (CTMP) or an equivalent product which is manufactured from sulphite pulp or kraft pulp, so-called chemical cellulose pulp. Cellulose fibres which have been stiffened chemically can also be used. Other particle-shaped constituents, for example conventional superabsorbent materials, thermoplastic binding fibres and other types of fibres, can also be incorporated into the dry-formed product. The dry-formed product which contains at least 70% flash-dried cellulose fibres is compressed into a sheet having a grammage of 100–1000 g/m² and a density of between 0.4–1.2 g/cm³ and is subsequently finely divided into the previously mentioned fragments having a length and width which is in the main 1–5 mm.

In the unprocessed state, dry-formed reel pulp has very good absorptive, dispersing and swelling properties, and the material has been found to be very suitable, when finely divided into fragments of a length and width of in the main about 1–5 mm, for being used, as a material having a high absorptive capacity, in hygiene articles. For example, the material exhibits a higher absorptive speed than that of conventional superabsorbents.

Fragments of dry-formed reel pulp have a structure which is similar to conventional cellulose materials, and the fragments thus bind more readily to the absorbent structure than do conventional superabsorbent materials, thereby helping to ensure, therefore, that these fragments will not be distributed in the production premises during the subsequent process for producing absorbent hygiene articles nor become redistributed in the finished hygiene article once it has been manufactured. In addition, fragments of dry-formed reel pulp enjoy a substantial cost advantage over conventional superabsorbent materials when the cost is calculated per quantity of absorbed liquid.

Normally, dry-formed reel pulp has a sheet strength which is sufficient for the product applications which are contemplated here. If the lattice strength should be found to be inadequate for certain product applications, it is possible to increase the said lattice strength by expediently reinforcing the structure by adding reinforcing fibres, binding fibres or binding agents to the cellulose fibre mixture.

In order to ensure that the fragments of dry-formed reel pulp have the desired properties, the dry-formed pulp mat must have a relatively high density. A suitable density is 0.4–1.2 g/cm³, preferably 0.5–1.1 g/cm³, and most preferably 0.8–1.0 g/cm³. A suitable grammage is between 100–1000 g/m², preferably 200–800 g/m², and most preferably 300–600 g/m².

Sheets of dry-formed cellulose pulp can, for example, be manufactured by forming a web of flash-dried fibres of paper pulp in accordance with the method which is described in European Patent EP 444 073.

Fibres of cellulose pulp have a curl value which describes the degree of curvature of the fibre. The fibres in dry-formed cellulose pulp preferably have a curl value of between 0.20 and 0.40. The curl value can be measured in accordance with the method which is described by B. D. Jordan and N. G. Nguyen in Papper och Trä (Paper and Wood) April 1986, page 313.

DESCRIPTION OF THE FIGURES

The invention will be described below in more detail with reference to the attached figures, of which

DESCRIPTION OF THE EXEMPLARY EMBODIMENT

The following test methods were used in order to evaluate the absorption properties.

In order to measure absorption speed, 4 volumes of in each case 28 ml of test liquid (0.9% solution of NaCl) were added at 20 min intervals to a test sample.

After each addition, the time in seconds which was taken for all the liquid to be absorbed was measured.

In order to measure rewetting, 4 volumes of in each case 28 ml of test liquid (0.9% solution of NaCl) were added at 20 min intervals to a test specimen. After the last volume of liquid had been absorbed, filter papers were placed over the wet zone and were loaded with a weight of 1.1 kg for 15 sec. The filter papers were weighed before and after the loading and the rewetting was recorded.

A Mitutoyo thickness gauge was used for measuring the thickness of the material when calculating density.

Figure 1:
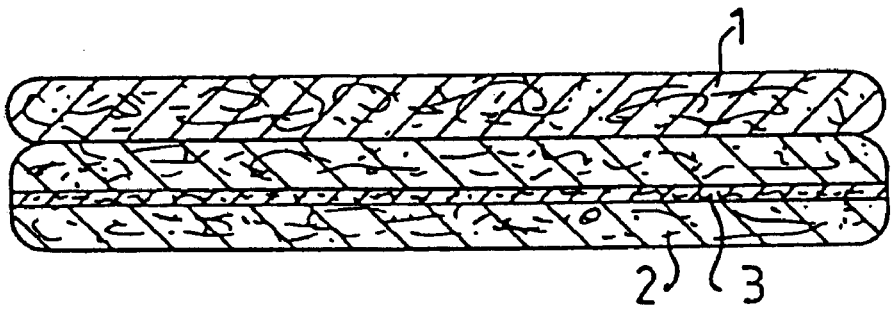
FIG. 1 shows a diagrammatic sketch of a reference product (ref. 1) which was used for comparative absorption measurements and which contains conventional cellulose pulp with which conventional superabsorbent materials have been admixed.

An absorbent structure in accordance with FIG. 1 was used as reference product No. 1. The structure consists of two layers, 1 and 2. The first layer 1 consists of a 50/50 mixture of chemithermomechanical cellulose pulp and chemical cellulose pulp having a grammage of 300 g/m² and a density of 0.12 g/m³. The second layer 2 consists of a 50/50 mixture of chemithermomechanical cellulose pulp and chemical cellulose pulp having a grammage of 750 g/m² and density of 0.17 g/m³. In the middle of layer 2 there is a layer 3 composed of a poly-acrylate-based superabsorbent material having a grammage of 200 g/m².

Figure 2:
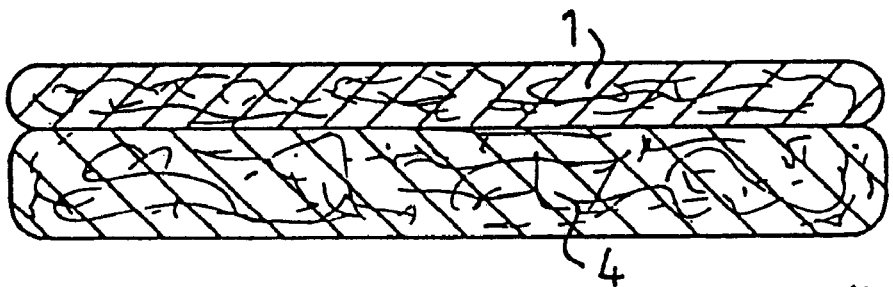
FIG. 2 shows a diagrammatic sketch of a reference product (ref. 2) which was used for comparative absorption measurements and which contains conventional cellulose pulp without any admixture of superabsorbent materials.

An absorbent structure according to FIG. 2 was used as reference product No. 2. The structure consists of two layers, 1 and 4. The first layer 1 consists of a 50/50 mixture of chemithermomechanical cellulose pulp and chemical cellulose pulp having a grammage of 300 g/m² and a density of 0.12 g/m³. The second layer 4 consists of a 50/50 mixture of chemithermomechanical cellulose pulp and chemical cellulose pulp having a grammage of 750 g/m² and a density of 0.17 g/m³.

Figure 3:
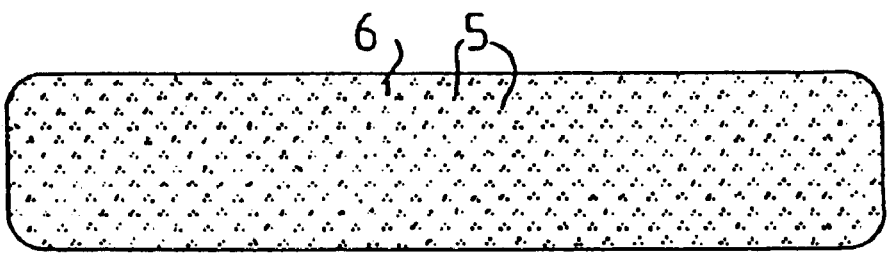
FIG. 3 shows a diagrammatic sketch of an absorbent structure (test) which was used for comparative absorption measurements and which contains conventional cellulose pulp with which a material of high absorptive capacity according to the invention has been admixed.

An absorbent structure according to FIG. 3 was used as the test product. The structure consists of a layer 5 having a grammage of 1500 g/m² and an average density of 0.17 g/m³. The layer 5 consists of a homogeneous mixture of chemical cellulose pulp containing a 35% admixture of material 6 according to the invention.

Figure 4:
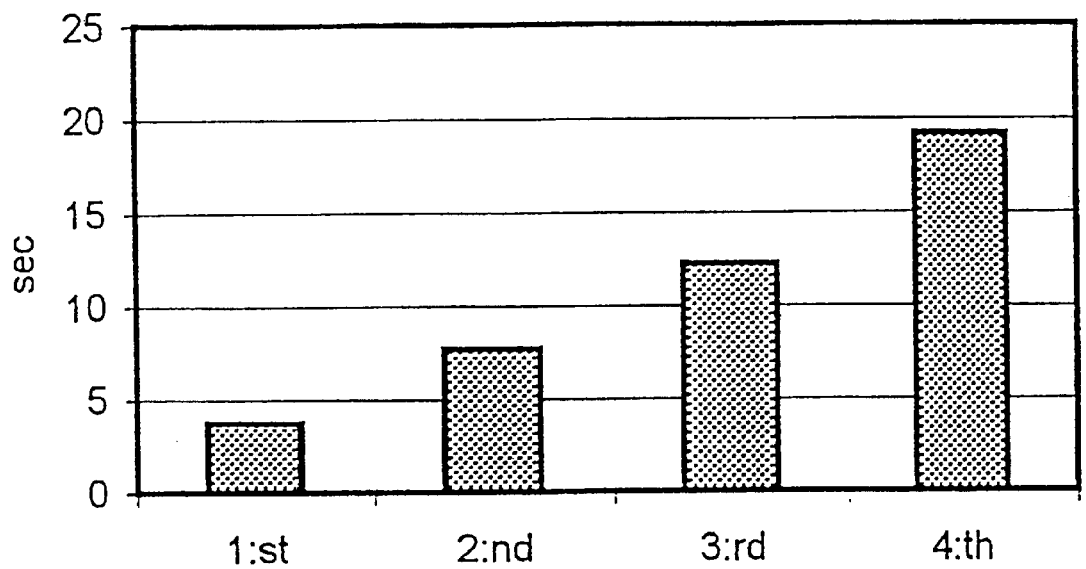
FIG. 4 shows the absorption speed in relation to repeated wetting in the case of reference product ref. 1.
Figure 5:
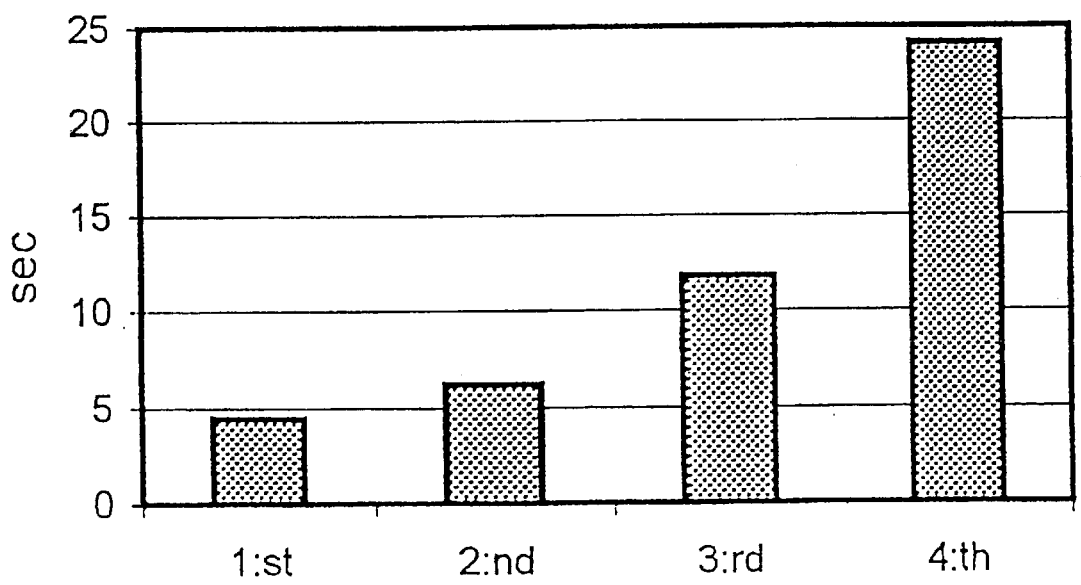
FIG. 5 shows the absorption speed in relation to repeated wetting in the case of reference product ref. 2.
Figure 6:
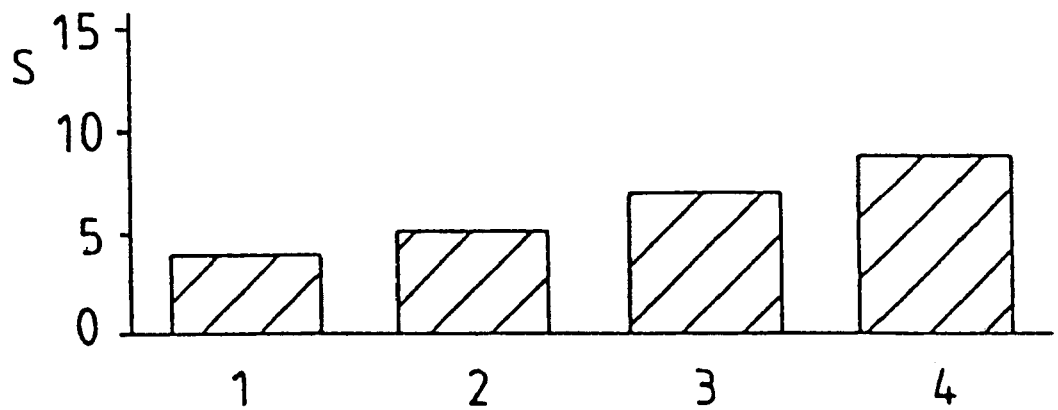
FIG. 6 shows the absorption speed in relation to repeated wetting in the case of the test product.

It is evident from FIGS. 4, 5 and 6 and Table 1 that an absorbent structure containing material according to the invention exhibits a substantially higher absorption speed in association with repeated wetting than do either of the reference products.

TABLE 1

| | Absorption speed, seconds/28 ml | | |
|---|---|---|---|
| Wetting | Ref. 1 | Ref. 2 | Test |
| 1st | 3.7 | 4.4 | 3.8 |
| 2nd | 7.7 | 6.2 | 4.9 |
| 3rd | 12.2 | 11.8 | 6.8 |
| 4th | 19.2 | 24.1 | 8.7 |

Figure 7:
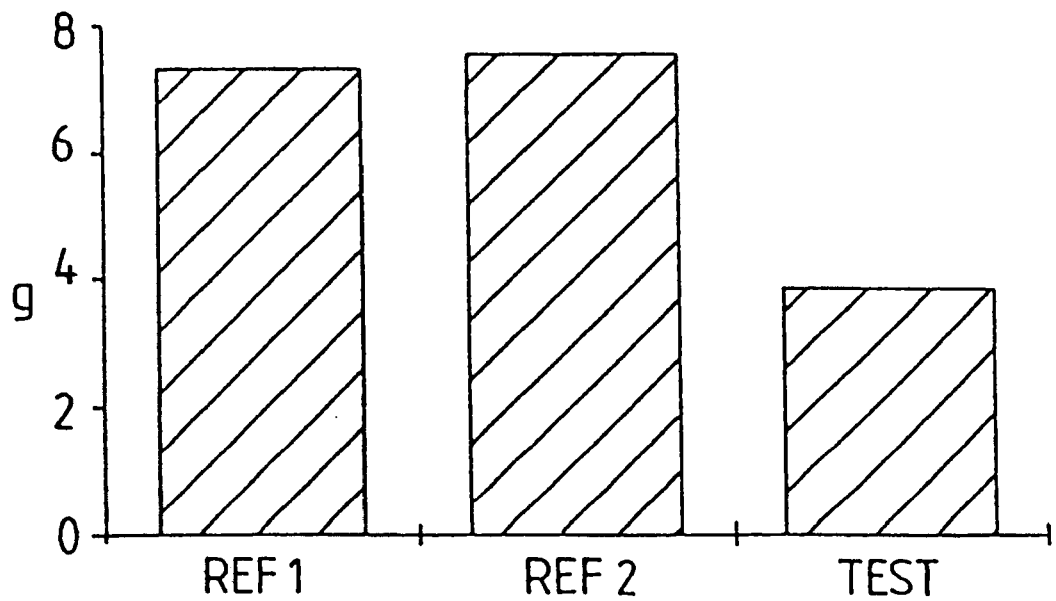
FIG. 7 shows the rewetting which occurs in the case of absorbent structures containing a material according to the invention and conventional cellulose pulp (test) as compared with that in the case of products containing conventional superabsorbent materials and conventional cellulose pulp (ref. 1) and conventional cellulose pulp alone (ref. 2), respectively.

It is evident from FIG. 7 and Table 2 that an absorbent structure containing material according to the invention exhibits substantially lower rewetting than do either of the reference products.

TABLE 2

| Rewetting, g | | |
|---|---|---|
| Ref. 1 | Ref. 2 | Test |
| 7.3 | 7.5 | 3.8 |

Naturally, the invention is not limited to the exemplary embodiment shown, but can, of course, be used for other embodiments within the scope of the subsequent patent claims.

What is claimed is:

1. A material having a high absorptive capacity and which is intended for use in an absorbent structure in an absorbent product such as a nappy, sanitary towel, and tampon, said material consisting of fragments (6) of a dry-formed sheet containing at least 70% flash-dried cellulose fibres and having a grammage of 100–1000 g/m$^2$ and a density of 0.4–1.2 g/cm$^3$, said fragments having a length and width of in the main 1–5 mm and the same grammage and density as the dry-formed sheet.

2. A material having a high absorptive capacity according to claim 1, wherein a sheet-forming material is compressed to a density of 0.5–1.1 g/cm$^3$ when the dry-formed sheet is manufactured.

3. A material having a high absorptive capacity according to claim 1, wherein a sheet-forming material is compressed to a density of 0.8–1.0 g/cm$^3$ when the dry-formed sheet is manufactured.

4. A material having a high absorptive capacity according to claim 1, wherein the dry-formed sheet has a grammage of 200–800 g/m$^2$.

5. A material having a high absorptive capacity according to claim 1, wherein the dry-formed sheet has a grammage of 300–600 g/m$^2$.

6. A material having a high absorptive capacity according to claim 1, wherein a sheet-forming material has a moisture content of between 3–20% calculated on a total weight of the web, when it is compressed during manufacture of the dry-formed sheet.

7. A material having a high absorptive capacity according to claim 6, wherein at least some of the fibres are cellulose fibres which have been stiffened chemically.

8. A material having a high a the sheet-forming material has a moisture content of between 4–18% calculated on a total weight of the web, when it is compressed during manufacture of the dry-formed sheet.

9. A material having a high absorptive capacity according to claim 1, wherein a sheet-forming material has a moisture content of between 11–16% calculated on a total weight of the web, when it is compressed during manufacture of the dry-formed sheet.

10. A material having a high absorptive capacity according to claim 1, wherein the cellulose fibres in the main consist of fibres of pulp produced by the chemithermomechanical route.

11. A material having a high absorptive capacity according to claim 10, wherein the chemithermomechanical pulp fibres have a curl value of between 0.20 and 0.40.

12. A material having a high absorptive capacity according to claim 1, wherein the cellulose fibres in the main consist of fibres of pulp produced by the chemical route. either on its own or together with another absorptive material, for example fluff pulp.

13. An absorbent product comprising a material having a high absorptive capacity in accordance with claim 14 and wherein over 50% of said fragments have a length and width from 1 mm to 5 mm wherein said absorbent product is one of a nappy, a sanitary towel, and a tampon.

14. An absorbent structure comprising a material having a high absorptive capacity in accordance with claim 1, and a second absorptive material.

15. A absorbent structure according to claim 14, wherein the proportion of the material having a high absorptive capacity is 10–70%.

16. A absorbent structure according to claim 14, wherein the proportion of the material having a high absorptive capacity is 20–50%.

17. A absorbent structure according to claim 14, wherein the proportion of the material having a high absorptive capacity is 30–40%.

18. A absorbent structure according to claim 14, comprising reinforcing agents, selected from the group consisting of binding agents, reinforcing fibres and thermoplastic binding fibres.

19. A absorbent product such as a nappy, sanitary towel, and incontinence protection having a liquid-permeable top layer, a bottom layer which is in the main liquid-impermeable, and an absorptive body between these layers, said product comprising an absorbent structure according to claim 14.

20. A absorbent product which is intended for absorbing blood, said product comprising an absorbent structure according to claim 14.

* * * * *